United States Patent
Zhao et al.

(10) Patent No.: US 10,586,324 B2
(45) Date of Patent: Mar. 10, 2020

(54) INSPECTION DEVICES AND METHODS FOR INSPECTING A CONTAINER

(71) Applicant: Nuctech Company Limited, Beijing (CN)

(72) Inventors: Ziran Zhao, Beijing (CN); Jianping Gu, Beijing (CN); Qian Yi, Beijing (CN); Bicheng Liu, Beijing (CN)

(73) Assignee: Nuctech Company Limited, Beijing (CN)

( * ) Notice: Subject to any disclaimer, the term of this patent is extended or adjusted under 35 U.S.C. 154(b) by 275 days.

(21) Appl. No.: 15/827,722

(22) Filed: Nov. 30, 2017

(65) Prior Publication Data

US 2018/0182085 A1 Jun. 28, 2018

(30) Foreign Application Priority Data

Dec. 26, 2016 (CN) .......................... 2016 1 1221485

(51) Int. Cl.
*G06T 7/00* (2017.01)
*G06T 7/73* (2017.01)
*G06T 5/20* (2006.01)
*G06T 5/50* (2006.01)
*G06T 5/00* (2006.01)
*G01V 5/00* (2006.01)
*G01N 23/04* (2018.01)

(52) U.S. Cl.
CPC ............ *G06T 7/001* (2013.01); *G01V 5/0016* (2013.01); *G06T 5/002* (2013.01); *G06T 5/20* (2013.01); *G06T 5/50* (2013.01); *G06T 7/0004* (2013.01); *G06T 7/74* (2017.01); *G01N 23/04* (2013.01); *G06T 2207/10028* (2013.01); *G06T 2207/10116* (2013.01); *G06T 2207/30112* (2013.01)

(58) Field of Classification Search
CPC ... G06T 7/74; G06T 2207/10116; G06T 5/50; G06T 5/002; G06T 227/10028; G06T 7/001; G01N 23/04
See application file for complete search history.

(56) References Cited

U.S. PATENT DOCUMENTS

2013/0235971 A1* 9/2013 Oreper .................. G01T 1/2985
378/19

FOREIGN PATENT DOCUMENTS

EP 1938752 A1 7/2008
EP 2401635 A2 1/2012
(Continued)

OTHER PUBLICATIONS

"European Application Serial No. 17204408.3, Extended European Search Report dated Sep. 18, 2018", (dated Sep. 18, 2018), 8 pgs.
(Continued)

*Primary Examiner* — Don K Wong
(74) *Attorney, Agent, or Firm* — Schwegman Lundberg & Woessner, P.A.

(57) ABSTRACT

The present disclosure discloses an inspection device and a method for inspecting a container. Transmission scanning is performed on the inspected container using a scanning device including a sparse area array detector to obtain scan data. Digital focusing is performed at a specific depth position in a depth direction. Defocused pixel values are filtered out to obtain a slice image at the specific depth position. It is judged whether dangerous articles or suspicious articles are included in the slice image.

15 Claims, 4 Drawing Sheets

(56) References Cited

FOREIGN PATENT DOCUMENTS

| JP | 2012518782 A | 8/2012 |
|----|---|---|
| JP | 2015520846 A | 7/2015 |
| WO | WO-2013126649 A2 | 8/2013 |
| WO | WO-2013165396 A1 | 11/2013 |
| WO | WO-2014121039 A1 | 8/2014 |

OTHER PUBLICATIONS

"Japanese Appliccation Serial No. 2017-232978, Notification of Refusal dated Dec. 5, 2018", w/ English Translation, (dated Dec. 5, 2018), 10 pgs.

Sisniega, A., et al., "Volumetric CT with sparse detector arrays (and application to Si-strip photon counters)", Physics in Medicine & Biology 61.1, (2015), 90-113.

"European Application Serial No. 10799287.7, Invitation pursuant to Rule 63(1) EPC dated May 14, 2018", (dated May 14, 2018), 4 pgs.

\* cited by examiner

INSPECTION DEVICES AND METHODS FOR INSPECTING A CONTAINER

CROSS-REFERENCE TO RELATED APPLICATION(S)

This application claims priority to the Chinese Patent Application No. 201611221485.2, filed on Dec. 26, 2016, entitled "INSPECTION DEVICES AND METHODS FOR INSPECTING A CONTAINER," which is incorporated herein by reference in its entirety.

TECHNICAL FIELD

The present disclosure relates to radiation inspection technology, and more particularly, to an inspection device and a method for inspecting a container.

BACKGROUND

The X-ray transmission technology is commonly used in inspection of cargos in a container in places such as airports, customs etc. The X-ray transmission technology utilizes a linear detector array to obtain a two-dimensional transmission image of the container. For example, X-rays are collimated to form a fan-shaped ray beam, which is transmitted through an inspected object for detection. When the object is stationary, the detector receives only a one-dimensional projection of the object on a ray layer. When the object moves in a direction perpendicular to the ray layer, all parts of the object sequentially pass through the ray beam, and the detector obtains a two-dimensional projection image of the whole object by line scanning. However, in the inspection manner described above, projections of the object in the container in a depth direction overlap together, which results in a loss of depth information. Especially for materials with light atomic numbers such as explosives and dangerous articles etc., grayscale attenuation after X-ray transmission is not obvious enough, which seriously affects recognition and identification of features such as a shape, a position etc. of such an object.

Common measures which are currently available for acquiring a three-dimensional transmission image are CT tomography and stereo matching technology etc. The CT tomography technology is complicated and expensive, and has a long imaging time, which limits its application in industrial real-time detection. In a process of stereo matching for an complex object, grayscale reconstruction and boundary processing are complex, the calculation complexity is also very large, and therefore the stereo matching is difficult to be applied in practice. Therefore, it is necessary to study other technologies to acquire three-dimensional imaging information of the object in the container.

SUMMARY

In view of one or more problems in the related art, an inspection device and inspection method for inspecting an inspected object such as a container is proposed.

According to an aspect of the present disclosure, there is proposed a method for inspecting a container, comprising steps of: performing transmission scanning on the inspected container using a scanning device including a sparse area array detector to obtain scan data; performing digital focusing at a specific depth position in a depth direction; filtering out defocused pixel values to obtain a slice image at the specific depth position; and judging whether dangerous articles or suspicious articles are included in the slice image.

In some embodiments, the digital focusing is performed according to the following equation:

$$\Delta x = (L-Z)/L \cdot \Delta D$$

wherein L is a horizontal distance from a ray source to a detector plane, $\Delta D$ represents an offset of a detection unit relative to a central line of the sparse area array detector, and $\Delta x$ represents an offset of an imaging position for an object point on the same projection ray at a depth Z.

In some embodiments, the sparse area array detector comprises: a first group of sparse area array detection units configured to detect a part of rays in a first energy range; and a second group of sparse area array detection units configured to detect a part of the rays in a second energy range, wherein the second energy range is higher than the first energy range.

In some embodiments, each detection unit in the sparse area array detector comprises a low-energy detection part, a filter, and a high-energy detection part.

In some embodiments, digital focusing is performed respectively at different depth positions and defocused pixel values are filtered out to obtain slice images at various positions, and the slice images are continuously played in an animation manner.

In some embodiments, the method comprises a step of: continuously adjusting, through an input apparatus, a depth position, wherein slice images at different depth values are played in an animation manner as the adjustment step is performed.

In some embodiments, the method further comprises a step of: creating a two-dimensional transmission image of an inspected object from detected data based on an offset of each detection unit in the sparse area array detector relative to a central line of the sparse area array detector.

In some embodiments, the method further comprises a step of: determining positions of the dangerous articles or suspicious articles in the container by combining the two-dimensional transmission image and the depth value corresponding to the slice image.

According to another aspect of the present disclosure, there is proposed an inspection device, comprising: a scanning device comprising a ray source and a sparse area array detector, configured to perform transmission scanning on an inspected container to obtain scan data; and a data processing device configured to perform digital focusing at a specific depth position in a depth direction, filter out defocused pixel values to obtain a slice image at the specific depth position, and judge whether dangerous articles or suspicious articles are included in the slice image.

In some embodiments, the sparse area array detector comprises: a first group of sparse area array detection units configured to detect a part of rays in a first energy range; and a second group of sparse area array detection units configured to detect a part of the rays in a second energy range, wherein the second energy range is higher than the first energy range.

In some embodiments, each detection unit in the sparse area array detector comprises a low-energy detection part, a filter, and a high-energy detection part.

In some embodiments, the data processing device is configured to perform the digital focusing according to the following equation:

$$\Delta x = (L-Z)/L \cdot \Delta D$$

wherein L is a horizontal distance from a ray source to a detector plane, ΔD represents an offset of a detection unit relative to a central line of the sparse area array detector, and Δx represents an offset of an imaging position for an object point on the same projection ray at a depth Z.

In some embodiments, the data processing device further comprises: an input apparatus configured to continuously adjust a depth position; and a display apparatus configured to play slice images at different depth values in an animation manner as the adjustment process is performed.

In some embodiments, the data processing device is configured to create a two-dimensional transmission image of an inspected object from detected data based on an offset of each detection unit in the sparse area array detector relative to a central line of the sparse area array detector.

In some embodiments, the data processing device is configured to determine positions of the dangerous articles or suspicious articles in the container by combining the two-dimensional transmission image and the depth value corresponding to the slice image.

With the above solution, it can be more accurately determined whether dangerous articles or suspicious articles are included in an inspected object, such as a container. In addition, a transmission image is combined with layered information, which can determine accurate positions of the dangerous articles or suspicious articles in the container.

BRIEF DESCRIPTION OF THE DRAWINGS

For a better understanding of the present disclosure, the present disclosure will be described in detail according to the following accompanying drawings.

DETAILED DESCRIPTION

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known structures, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the term "and/or" used herein means any and all combinations of one or more listed items.

In view of one or more problems in the related art, the embodiments of the present disclosure propose a technique for performing imaging inspection using a sparse area array detector. An inspected object is scanned using an array of detectors which are discretely distributed in a horizontal direction, and then the scanned image is digitally focused, to obtain images of the object in different layers in a depth direction, thus obtaining layered information of the inspected object. In addition, in some embodiments, in order to improve the spatial resolution effect of the reconstruction in the depth direction, a multi-energy detector is used to make full use of low-energy components in X-rays to recognize a thinner object. In other embodiments, the layered depth information may be combined into a two-dimensional transmission image to realize three-dimensional spatial positioning of the dangerous articles/suspicious articles in the container.

According to the embodiments of the present disclosure, the layered information of the inspected object in the container in the depth direction can be obtained by using the area array detector in a sparse distribution and the imaging method. In addition, the multi-energy detector can make full use of low-energy components in the X-rays to inspect the thinner substances, thereby improving the spatial resolution capability. In addition, the depth information and the X-ray transmission image are combined to obtain a three-dimensional image of the inspected object and positioning of dangerous articles.

Figure 1:
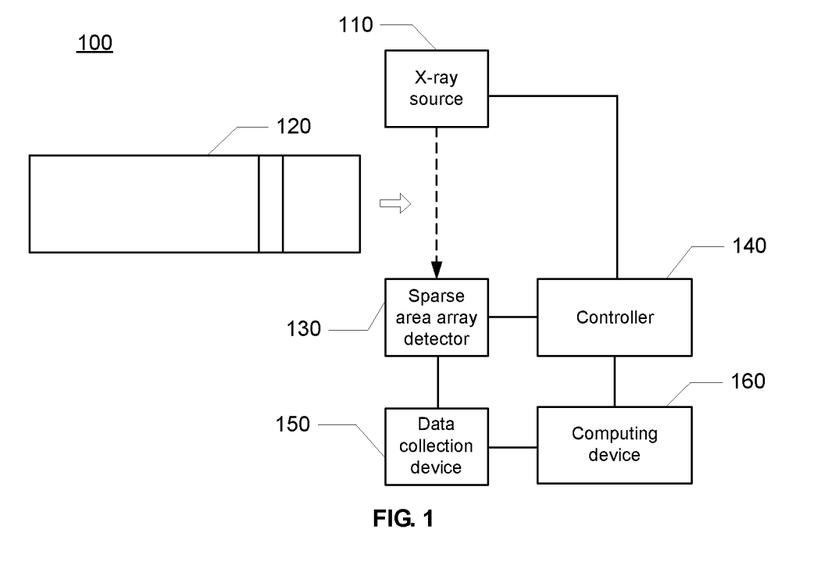
FIG. 1 illustrates a structural diagram of an inspection device according to an embodiment of the present disclosure.

FIG. 1 illustrates a structural diagram of an inspection device according to an embodiment of the present disclosure. As shown in FIG. 1, an inspection device 100 according to an embodiment of the present disclosure comprises an X-ray source 110, a sparse area array detector 130, a data collection apparatus 150, a controller 140, and a computing device 160, and performs security inspection on an inspected object 120 such as a container truck etc., for example, judges whether there are dangerous articles or suspicious articles included therein. Although the detector 130 and the data collection apparatus 150 are separately described in this embodiment, it should be understood by those skilled in the art that they may also be integrated together as an X-ray detection and data collection device.

According to some embodiments, the X-ray source 110 may be an isotope, or may also be an X-ray machine, an accelerator, etc. The X-ray source 110 may be a single-energy ray source or a dual-energy ray source. this way, transmission scanning is performed on the inspected object 120 through the X-ray source 110, the sparse area array detector 150, the controller 140, and the computing device 160 to obtain detection data. For example, in a process that the inspected object 120 moves, an operator controls the controller 140 to transmit an instruction through a man-machine interface of the computing device 160 to instruct the X-ray source 110 to emit rays, which are transmitted through the inspected object 120 and are then received by the sparse area array detector 130 and the data collection device 150. Further, data is processed by the computing device 160 to obtain a transmission image on the one hand and layered information of the inspected object in a depth direction on the other hand. In addition, slice information on a certain layer may also be obtained, to provide a priori knowledge for subsequent inspection of dangerous articles/suspicious articles. In this way, positions of the suspicious articles in the container may be determined, for example, by comparing characteristic values, such as atomic numbers etc., so that three-dimensional positioning of the suspicious articles can be quickly performed to facilitate an inspector to find the positions of the dangerous/suspicious articles.

Figure 2:
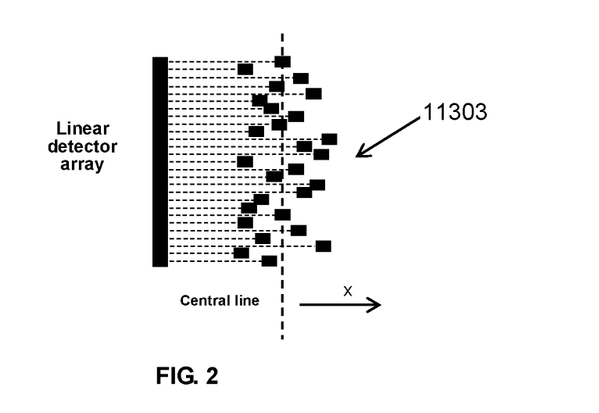
FIG. 2 is a structural diagram illustrating a sparse area array detector included in the inspection device shown in FIG. 1.

FIG. 2 is a structural diagram illustrating a sparse area array detector included in the inspection device shown in FIG. 1. According to the embodiments of the present disclosure, the sparse area array detector 130 is used. Compared with a linear array detector, it can be considered that the sparse area array detector 130 is formed in a sparse array distribution form by arranging various detection units of the linear array detector to be distributed randomly in a horizontal direction (for example, a moving direction of an object). As shown in FIG. 2, various detection units are distributed randomly with respect to a central line of the sparse area array detector.

According to the embodiments of the present disclosure, in the X-ray fluoroscopy technology, an object is irradiated with X-rays to obtain an image of internal conditions of the related object through difference in absorptions of the rays by internal substances, so as to inspect cargos. If the linear detector array is used, a two-dimensional transmission image of an object in a container is obtained. Projections of the object in a depth direction overlap together, which causes a loss of resolution information in the depth direction, thereby affecting people's identification and recognition of features of the object, such as a shape and a position etc. According to the embodiments of the present disclosure, the depth information of the object in the container may be obtained by using the sparse area array detector, so that a three-dimensional image is formed, thereby greatly improving the accuracy and efficiency of security inspection of the container. For example, layered images of the inspected object may be obtained by using a random discrete detector array instead of the linear detector and processing data using an imaging algorithm.

Figure 3:
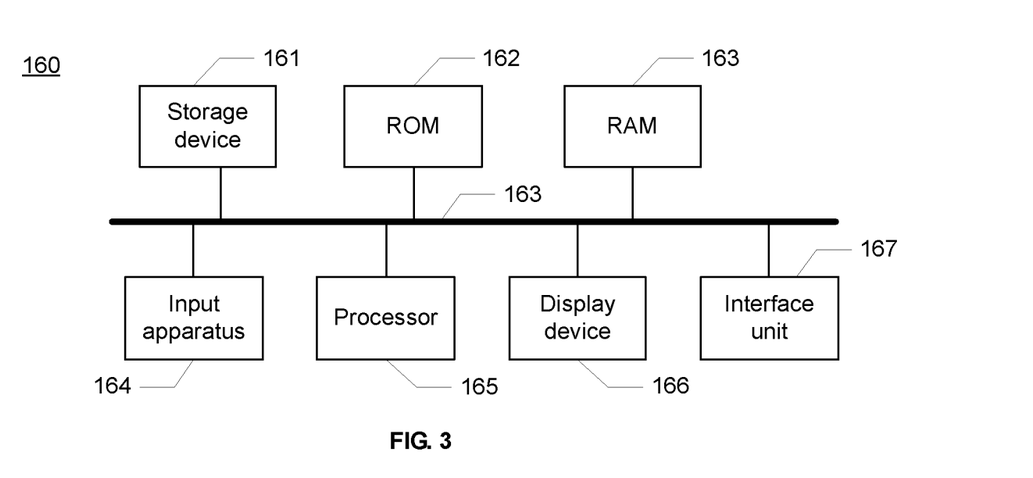
FIG. 3 is a structural diagram illustrating a computing device included in the inspection device shown in FIG. 1.

FIG. 3 illustrates a structural diagram of the computing device shown in FIG. 1. As shown in FIG. 3, a signal detected by a sparse area array detector 130 is collected by a data collector, and data is stored in a memory 161 through an interface unit 167 and a bus 163. A Read Only Memory (ROM) 162 stores configuration information and programs of a computer data processor. A Random Access Memory (RAM) 163 is configured to temporarily store various data when a processor 165 is in operation. In addition, computer programs for performing data processing, such as a substance recognition program and an image processing program etc., are also stored in the memory 161. The internal bus 163 connects the memory 161, the ROM 162, the RAM 163, an input apparatus 164, the processor 165, a display apparatus 166, and the interface unit 167 described above.

After a user inputs an operation command through the input apparatus 164 such as a keyboard and a mouse etc., instruction codes of a computer program instruct the processor 165 to perform a predetermined data processing algorithm. After a result of the data processing is acquired, the result is displayed on the display apparatus 166 such as a Liquid Crystal Display (LCD) display etc. or is directly output in a form of hard copy such as printing etc.

Figure 4:
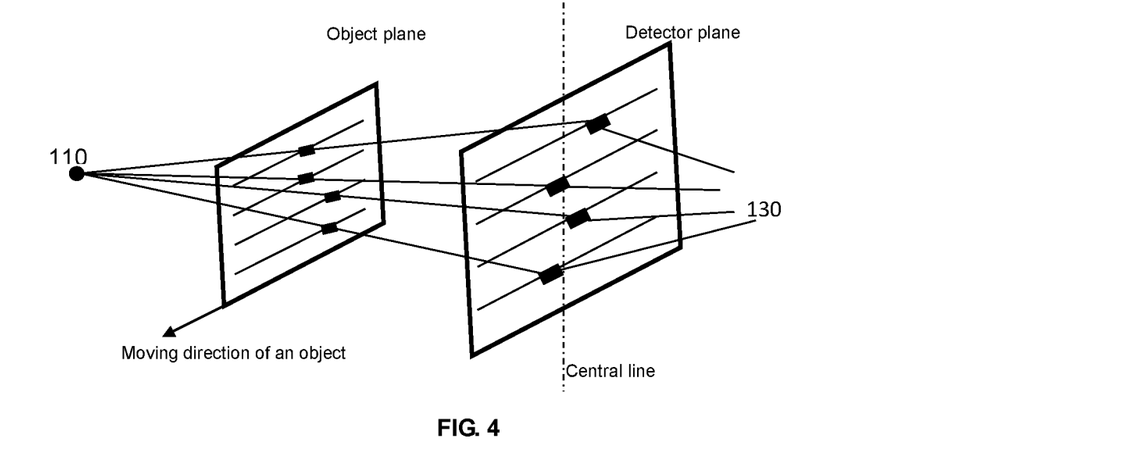
FIG. 4 is a diagram illustrating an imaging process according to an embodiment of the present disclosure.
Figure 5:
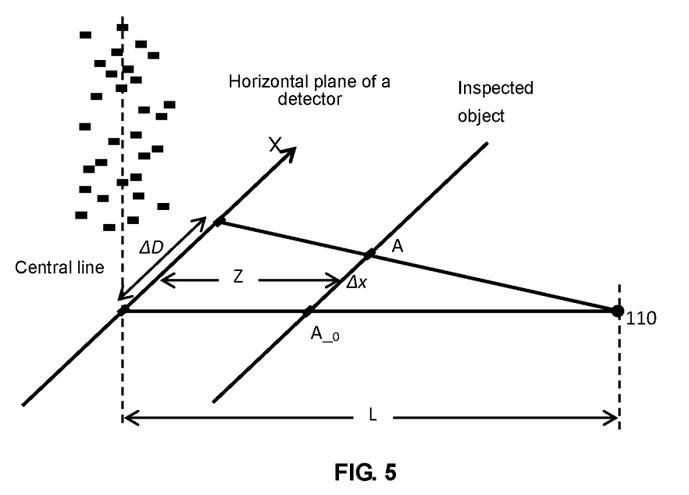
FIG. 5 is a diagram illustrating an imaging principle according to an embodiment of the present disclosure.

FIG. 4 is a diagram illustrating an imaging process according to an embodiment of the present disclosure. As shown in FIG. 4, detection units which are arranged vertically in a line are separated horizontally and each detector has a random horizontal displacement relative to a central line. Thus, for the rays emitted by the ray source 110, a group of rays which pass through different positions of an object are received by the detector array 130 at the same time. The principle of imaging under a sparse area array detector is shown in FIG. 5. It is assumed that the rays are scanned in an x-axis direction, various detection units are randomly and discretely distributed within a certain range in a horizontal direction, and each detection unit of the sparse area array detector has a random given horizontal displacement $\Delta D$ relative to the central line of the detector array (which can be known when the detector is designed). In this case, a certain point A_0 on an object which has a horizontal distance Z from a detector plane may appear in a projection image with a lag distance $\Delta x$ relative to a point on the object (as indicated by point A in FIG. 5) for a linear detector:

$$\Delta x = (L-Z)/L \cdot \Delta D \quad (1)$$

In the above equation (1), L is a horizontal distance from an accelerator target to the detector plane. It can be known from the above equation (1) that, when the detector crystal has a constant offset $\Delta D$, imaging positions for object points on the same projection ray emitted by the ray source 110 at different depths Z have different offsets $\Delta x$.

According to the embodiments of the present disclosure, the above reconstruction method is reflected on the image as making the object which originally has a clear structure become a bunch of cluttered scatter points. However, this clutter may be corrected by positions of the detection units. A structure at a displacement $\Delta x$ on a certain plane of an object which has a distance Z from the detector plane may appear in the image with a lag distance $\Delta D$ relative to the central line of the detectors. Therefore, as long as a scan line of a detection unit is moved forward by a distance $\Delta D$, the scan line may be aligned with the central line. If all the detectors are aligned proportionally with the central line, the structure on the plane of the object can be clearly imaged, that is, "digitally focused." If all detector pixels are corrected in accordance with the horizontal displacement $\Delta D$ to align with the central line, a profile of the object at this depth position can be clearly imaged, with points on other layers being random noises. The detector may be corrected by different horizontal displacements $\Delta D$ to perform layered imaging on the object at different depths Z. That is, object points on a specific depth layer Z should conform to the above equation, and imaging points which are not on this layer may appear to be defocused. Therefore, digital focusing, de-noising, filtering etc. may be performed to extract an image belonging to the layer Z.

According to some embodiments, digital focusing may be separately performed at different depth positions, defocused pixel values may be filtered out to obtain slice images at various positions, and the slice images may be continuously played in an animation manner. For example, a total of ten slice images at depth positions Z1, Z2, . . . and Z10 are respectively obtained, and are then played in an animation manner or at a user-defined speed. As another example, the depth position may be continuously adjusted through the input apparatus 164, and the slice images at different depth values are played by the calculation device 160 in an animation manner as the depth value changes.

Figure 6:
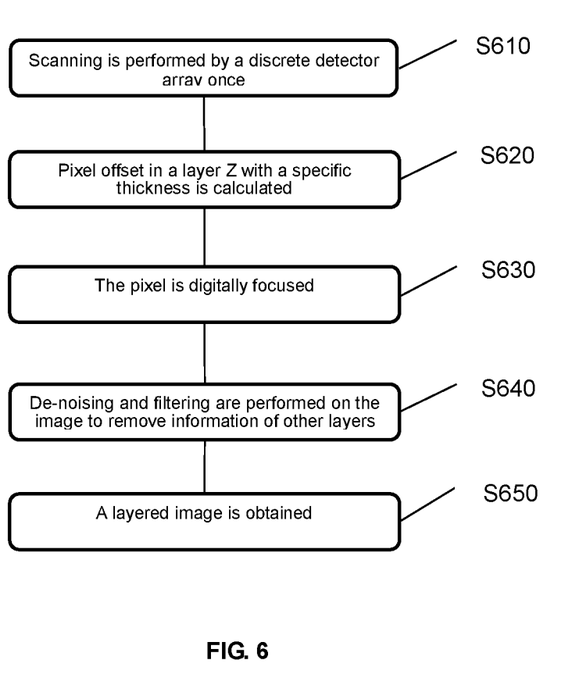
FIG. 6 is a schematic flowchart illustrating an imaging process according to an embodiment of the present disclosure.

FIG. 6 is a schematic flowchart illustrating an imaging process according to an embodiment of the present disclosure. As shown in FIG. 6, in step S610, for example, an operator controls the controller 140 to transmit an instruction through a man-machine interface of the computing device 160 to instruct the X-ray source 110 to emit rays, which are transmitted through the inspected object 120 and are then received by the sparse area array detector 130 and the data collection device 150. In this way, transmission scanning is performed on the inspected object such as a container etc. once.

Next, in step S620, the data is processed by the computing device 160, for example, a pixel offset $\Delta x$ in a layer Z with a specific thickness is calculated. Then, in step S630, the pixel is digitally focused, for example, with reference to the equation (1) above, to calculate the focused pixel value at a particular position Z. All detector pixels are corrected by a horizontal displacement $\Delta D$ to align with the central line, and thereby a profile of the object at this depth position can be clearly imaged, and points on other layers appear to be defocused and may be construed as random noises.

Then, in step S640, operations such as de-noising, filtering, etc. are performed on the image to remove defocused pixel values of other layers except for the layer at the position Z. For example, those skilled in the art can select a suitable de-noising algorithm according to different scenarios to perform de-noising on the focused image and eliminate the influence of the defocused pixel points. In this way, in step S650, a layered image, that is, a slice image at the position Z, is obtained.

In addition, a thickness may be calculated by sampling to achieve layered detection of the object in the container. In fact, each of objects in the container has a certain thickness, and therefore thicknesses of layers and a number of the layers may be selected to be in a suitable range, which can not only ensure the layered imaging effect, but also can facilitate the design of the detector distribution.

In addition, according to some embodiments of the present disclosure, a multi-energy detector may be used. For example, the sparse area array detector may comprise a high-energy detector group and a low-energy detector group. For example, low-energy may refer to an energy range from 3 MeV to 5 MeV, and high-energy may refer to an energy range from 7 MeV to 9 MeV. Those skilled in the art can set high and low-energy range values according to practical requirements. According to the absorption characteristics of X rays by the detector, a thinner detector may have a certain improvement on the discrimination effect between materials with medium and low atomic numbers and thinner materials with a high atomic number. In order to take full advantage of these features, a multi-energy detector can be designed.

Figure 7:
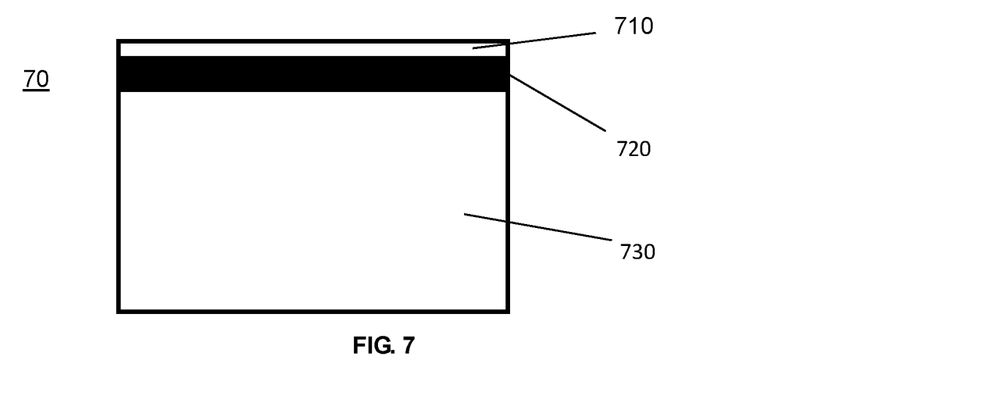
FIG. 7 illustrates a structural diagram of detection units of a pseudo-dual-energy detector used in an embodiment of the present disclosure.

FIG. 7 illustrates a structural diagram of detection units of a pseudo-dual-energy detector 700 according to an embodiment of the present disclosure. As shown in FIG. 7, a thinner detector is placed in front of a high-energy detector as a low-energy detector to detect low-energy components of an energy spectrum. As shown in FIG. 7, a thinner low-energy detector crystal 710 (for example, CsI (TI) with a thickness of 0.3 mm) is close to the ray source, and is followed a metal filter 720 (for example, Cu with a thickness of 0.5 mm) sandwiched between two layers of detectors, which is followed by a thicker high-energy detector crystal 730 (for example, CsI (TI) with a thickness of 4 mm).

According to an embodiment of the present disclosure, the ray source 110 may be implemented by a dual-energy accelerator or a single-energy accelerator. It should be noted that due to the use of the pseudo-dual-energy detector, the accelerator used is not limited to the dual-energy accelerator, and the single-energy X-ray accelerator may also be used. The X-rays are collimated to form a fan-shaped ray beam, which passes through the inspected object and reaches a position sensitive detector array. When the object moves in a direction perpendicular to a ray plane, all parts of the object sequentially pass through the ray beam, and the detector obtains a projection image of the whole object by means of line scanning. If material information of the object in the container is further to be acquired, the dual-energy accelerator may be used to obtain a transmission image and a material image, which are then combined with the depth layered information obtained by the sparse area array detector to form a three-dimensional structure and material image.

According to an embodiment of the present disclosure, a two-dimensional transmission image of the container may be obtained by the computing device 160. For example, the two-dimensional transmission image may be restored by alignment with the central line in a condition that the arrangement of the sparse detector is known.

Figure 8:
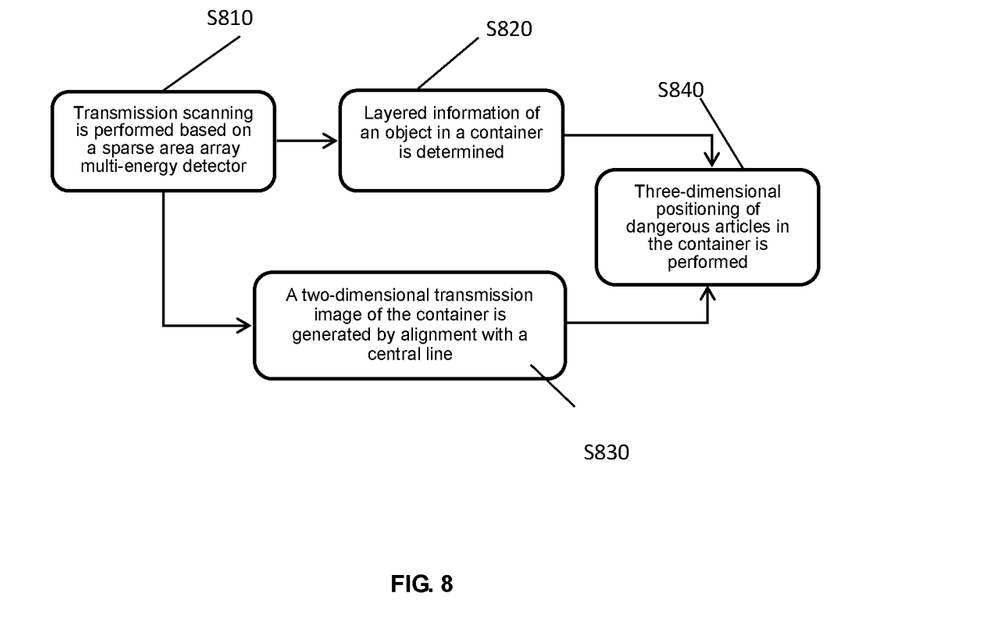
FIG. 8 illustrates a flowchart of positioning dangerous articles in a container according to an embodiment of the present disclosure.

FIG. 8 is a flowchart of three-dimensional positioning of dangerous articles in a container. As shown in FIG. 8, in step S810, transmission scanning is performed on an inspected object using a sparse area array detector to obtain scan data.

Then, in step S820, corresponding slice images are determined at different depths Z, and when there are dangerous articles or suspicious articles in a slice image, a corresponding depth value Z is recorded. In step S830, a two-dimensional transmission image may be restored by alignment with a central line in a condition that arrangement of the sparse detector is known. In step S840, three-dimensional positions of dangerous articles or suspicious articles are determined using the recorded depth value Z and the two-dimensional transmission image. For example, horizontal and vertical coordinates of the dangerous articles or suspicious articles are obtained by determining positions of the dangerous articles or suspicious articles in the two-dimensional transmission image, and are then combined with the depth value Z to determine three-dimensional coordinates of the dangerous articles or suspicious articles. According to other embodiments, if the accelerator used is a dual-energy accelerator, a three-dimensional material recognition image may also be reconstructed.

Although the flow of the method according to the present disclosure has been described in a specific order in the above embodiments, it should be understood by those skilled in the art that some steps may be performed in another order or may be performed in parallel.

In the embodiments of the present disclosure described above, layered information of an inspected object is acquired through the detection units which are sparsely distributed and the reconstruction method. With the multi-energy detector, better detection of substances with a low-atomic number and thinner substances can be realized. The depth layered information and X-ray transmission images are combined to obtain a three-dimensional image of the inspected object and positioning of dangerous articles. In this way, the defect that in the conventional X-ray transmission system, information in a depth direction overlap due to the use of the linear detection array can be remedied, and the accuracy, efficiency and image display effect of the security inspection of the container can be improved.

The foregoing detailed description has set forth various embodiments of the inspection device and the inspection method via the use of diagrams, flowcharts, and/or examples. In a case that such diagrams, flowcharts, and/or examples contain one or more functions and/or operations, it will be understood by those skilled in the art that each function and/or operation within such diagrams, flowcharts or examples may be implemented, individually and/or collectively, by a wide range of structures, hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

We claim:

1. A method for inspecting a container, comprising steps of:
    performing transmission scanning on the inspected container using a scanning device including a sparse area array detector to obtain scan data;
    performing digital focusing at a specific depth position in a depth direction;
    filtering out defocused pixel values to obtain a slice image at the specific depth position; and
    judging whether dangerous articles or suspicious articles are included in the slice image.

2. The method according to claim 1, wherein the digital focusing is performed according to the following equation:

$$\Delta x = (L-Z)/L \cdot \Delta D$$

wherein L is a horizontal distance from a ray source to a detector plane, $\Delta D$ represents an offset of a detection unit relative to a central line of the sparse area array detector, and $\Delta x$ represents an offset of an imaging position for an object point on the same projection ray at a depth Z.

3. The method according to claim 1, wherein the sparse area array detector comprises:
    a first group of sparse area array detection units configured to detect a part of rays in a first energy range; and
    a second group of sparse area array detection units configured to detect a part of the rays in a second energy range, wherein the second energy range is higher than the first energy range.

4. The method according to claim 1, wherein each detection unit in the sparse area array detector comprises a low-energy detection part, a filter, and a high-energy detection part.

5. The method according to claim 1, wherein digital focusing is performed respectively at different depth positions and defocused pixel values are filtered out to obtain slice images at various positions, and the slice images are continuously played in an animation manner.

6. The method according to claim 1, comprising a step of:
    continuously adjusting, through an input apparatus, a depth position,
    wherein slice images at different depth values are played in an animation manner as the adjustment step is performed.

7. The method according to claim 1, further comprising a step of:
    creating a two-dimensional transmission image of an inspected object from detected data based on an offset of each detection unit in the sparse area array detector relative to a central line of the sparse area array detector.

8. The method according to claim 7, further comprising a step of:
    determining positions of the dangerous articles or suspicious articles in the container by combining the two-dimensional transmission image and the depth value corresponding to the slice image.

9. An inspection device, comprising:
    a scanning device comprising a ray source and a sparse area array detector, configured to perform transmission scanning on an inspected container to obtain scan data; and
    a data processing device configured to perform digital focusing at a specific depth position in a depth direction, filter out defocused pixel values to obtain a slice image at the specific depth position, and judge whether dangerous articles or suspicious articles are included in the slice image.

10. The inspection device according to claim 9, wherein the sparse area array detector comprises:
    a first group of sparse area array detection units configured to detect a part of rays in a first energy range; and
    a second group of sparse area array detection units configured to detect a part of the rays in a second energy range, wherein the second energy range is higher than the first energy range.

11. The inspection device according to claim 9, wherein each detection unit in the sparse area array detector comprises a low-energy detection part, a filter, and a high-energy detection part.

12. The inspection device according to claim 9, wherein the data processing device is configured to perform the digital focusing according to the following equation:

$$\Delta x = (L-Z)/L \cdot \Delta D$$

wherein L is a horizontal distance from a ray source to a detector plane, $\Delta D$ represents an offset of a detection unit relative to a central line of the sparse area array detector, and $\Delta x$ represents an offset of an imaging position for an object point on the same projection ray at a depth Z.

13. The inspection device according to claim 9, wherein the data processing device further comprises:
an input apparatus configured to continuously adjust a depth position; and
a display apparatus configured to play slice images at different depth values in an animation manner as the adjustment process is performed.

14. The inspection device according to claim 9, wherein the data processing device is configured to create a two-dimensional transmission image of an inspected object from detected data based on an offset of each detection unit in the sparse area array detector relative to a central line of the sparse area array detector.

15. The inspection device according to claim 14, wherein the data processing device is configured to determine positions of the dangerous articles or suspicious articles in the container by combining the two-dimensional transmission image and the depth value corresponding to the slice image.

* * * * *